US006682478B2

(12) United States Patent
Nakamura

(10) Patent No.: US 6,682,478 B2
(45) Date of Patent: Jan. 27, 2004

(54) ENDOSCOPE APPARATUS WITH AN INSERTION PART HAVING A SMALL OUTER DIAMETER WHICH INCLUDES AND OBJECT OPTICAL SYSTEM

(75) Inventor: Minoru Nakamura, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/778,784

(22) Filed: Feb. 8, 2001

(65) Prior Publication Data
US 2002/0161278 A1 Oct. 31, 2002

(51) Int. Cl.[7] .................................................. A61B 1/05
(52) U.S. Cl. ....................................... 600/111; 600/176
(58) Field of Search ............................... 600/160, 109, 600/129, 167, 168, 176, 166, 111; 359/784, 762, 755

(56) References Cited

U.S. PATENT DOCUMENTS

| 5,515,208 A | * | 5/1996 | Yamamoto et al. | ......... 359/740 |
|---|---|---|---|---|
| 5,689,365 A | * | 11/1997 | Takahashi | .................... 359/362 |
| 5,703,724 A | * | 12/1997 | Miyano | ....................... 359/660 |
| 5,743,846 A | | 4/1998 | Takahashi et al. | |
| 5,891,015 A | * | 4/1999 | Strahle | ........................ 600/160 |
| 5,971,915 A | | 10/1999 | Yamamoto et al. | |
| 6,243,217 B1 | * | 6/2001 | Nagaoka | ..................... 359/793 |

FOREIGN PATENT DOCUMENTS

JP    11-109257    4/1999

* cited by examiner

Primary Examiner—John P. Leubecker
(74) Attorney, Agent, or Firm—Westerman, Hattori, Daniels & Adrian, LLP

(57) ABSTRACT

An endoscope apparatus has an object optical system to conduct measurements or stereoscopic-vision observations. The object optical system arranges in order from an object side to an image side, a first unit, a second unit, a third unit, and an image pickup unit. The first unit includes negative lenses, the second unit includes first positive lenses, wherein the first positive lenses form no real image within the second and third units. The third unit includes second positive lenses, and the image pickup unit includes a single image pick up device.

18 Claims, 9 Drawing Sheets

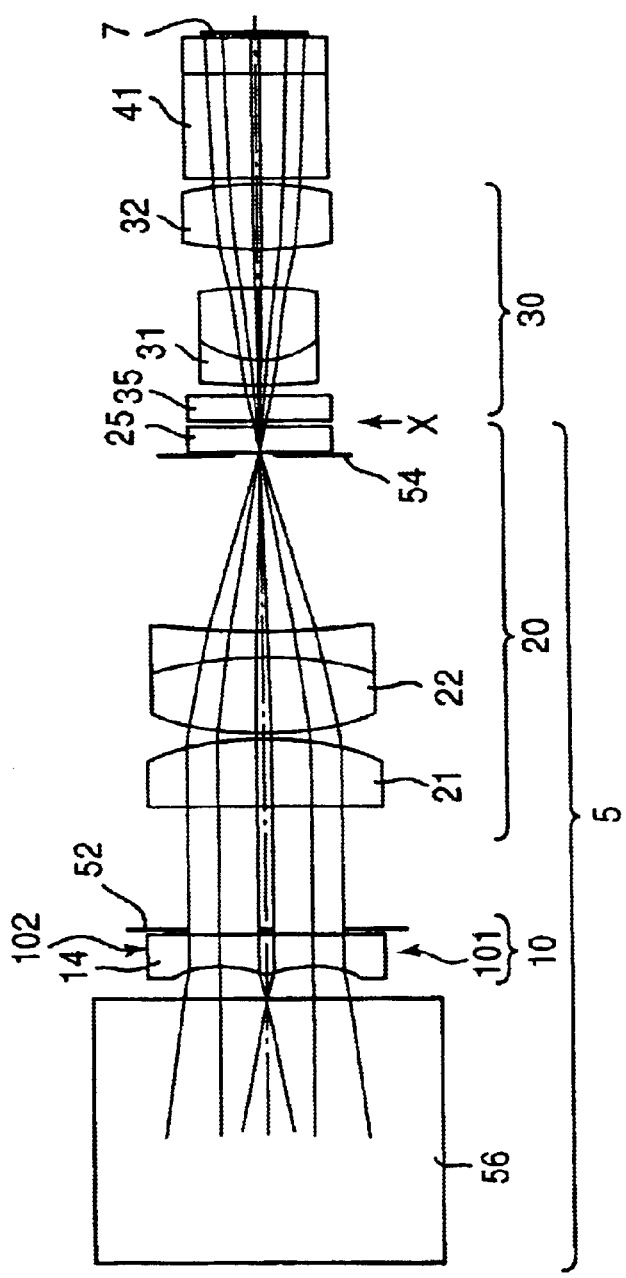
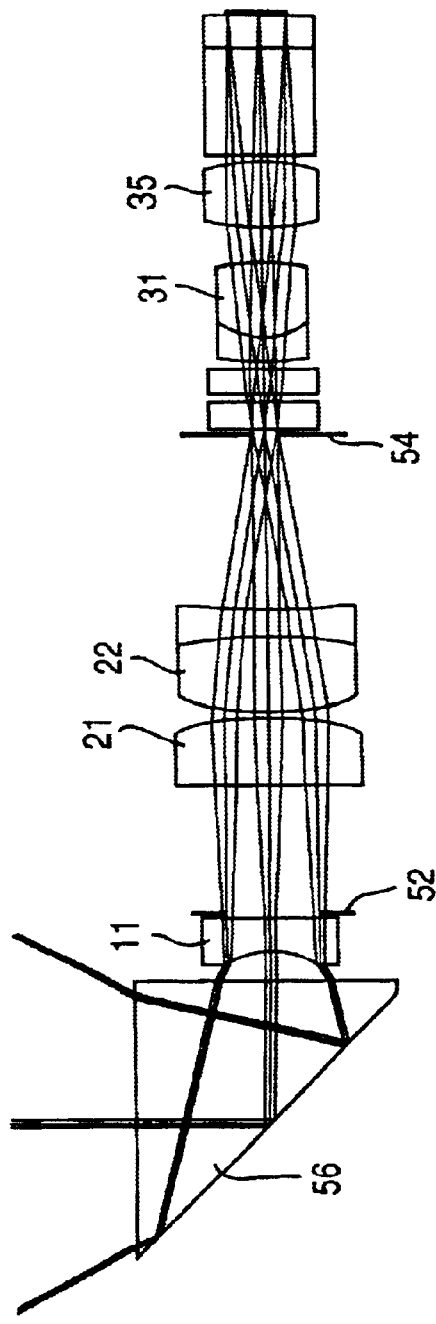
FIG. 3
FIG. 4

ENDOSCOPE APPARATUS WITH AN INSERTION PART HAVING A SMALL OUTER DIAMETER WHICH INCLUDES AND OBJECT OPTICAL SYSTEM

FIELD OF THE INVENTION

The present invention relates to an endoscope apparatus with an insertion part having a small outer diameter which includes an object optical system to conduct measurements or stereoscopic-vision observations.

BACKGROUND OF THE INVENTION

Applications of stereoscopic-vision and measurement endoscopes include, for instance, the following fields: inspection of supply pipes of cooling water in nuclear power stations; inspection of turbine blades of steam generators in power plants; and inspection of aircraft engines. In medical applications, they may also be applied to surgery using an endoscope.

In any case, flaws and cracks of related parts, or size and depth of an affected area can be measured without disassembly or laparotomy, and its servicing or operation can be effectively conducted in safety by use of stereoscopic-vision.

Conventional stereoscopic-vision and measurement endoscopes will be described with reference to FIGS. 8 to 13. Heretofore, in order to obtain a parallax for the stereoscopic-vision and measurement, it has been widely known to align two identical right and left optical systems in parallel with each other. However, an inevitable error between the right and left optical systems does not allow the right and left images to be identical to each other. In the stereoscopic-vision, the resulting difference between the right and left images produces a fusion-image of the right and left images for an observer, which causes observer's fatigue. This difference also causes a measurement error in a measurement. Thus, in order to lessen the fatigue and error, it is required to minimize the number of parts in the right and left optical systems. The following two prior arts references provide a means to solve this: Japanese Patent Laid-Open Publication No. Hei 8-122665 (U.S. Pat. No. 5,743,846) shown in FIG. 9; and Japanese Patent Laid-Open Publication No. Hei 11-006967 (U.S. Pat. No. 5,971,915) shown in FIG. 10.

These prior arts references each provide right and left optical systems partially having the same right and left parts, which are expected to reduce the error. However, a brightness diaphragm 55 of the prior arts comprises two apertures each of which corresponds to the respective objective lenses positioned in parallel. This involves a disparity of each aperture to the corresponding optical axis and an error between the respective right and left apertures, which leads to an error between the right and left images.

A prior art reference in which a brightness diaphragm has one unified aperture is disclosed by Japanese Patent Laid-Open Publication No. Hei 11-109257 shown in FIG. 8. In this prior art reference, a brightness diaphragm 54 having one aperture may solve the above-mentioned problem. However, focusing a real image on the end surface 9 of each objective lens runs into following three problems.

First, a combined dimension of objective lenses 121, 122 and relay lenses 50, 54, 6 in the direction of an optical axis is lengthened, because the real images are formed by the objective lenses 121, 122 which have a positive focal distance and are positioned in parallel at a top of the endoscope, and the dimension of these objective lenses directly makes the overall length of the endoscope longer. Further, a rigid section (i.e. unbendable section) will be undesirably lengthened.

Second, if some contamination intrudes and is attached on the end surface 9 of the objective lens in the manufacturing process, the contamination overlapped with the real image is reflected into the image, which undesirably disturbs the stereoscopic-vision and measurement.

Third, since the real image is focused into a final image on an image pickup device by relaying the real image, the real image 9 directed to an axial direction of the endoscope is inverted and formed as the image directed outward at the image pickup device 7. Thus, the right-and-left state of a displayed image on a monitor will be in a state of counter-changing the right and left which are generally recognized by humans. Specifically, an image to be fundamentally monitored by a right eye will be an image for a left eye. Consequently, this prior art undesirably provides a reverse-stereoscopic-vision in which information in the direction of stereopsis is reversed for the right and left.

Further, the prior art is a top afocal adapter type of endoscope. FIG. 11 shows a general view of the top afocal adapter type of endoscope. FIG. 13 is a sectional view showing an objective optical system in the top section of the endoscope. As shown in FIGS. 11 to 13, a top afocal adapter 5 is detachable from an endoscope body 4. Referring to FIG. 13, a master lens 6 is provided in the endoscope body 4, and adjusts to make a focal point locate approximately at infinity to an image pickup device 7. A top afocal adapter 5 may have different field angles and line of sights suitable for observation purposes, and also may be detachably at a position X on the object side of the master lens. FIG. 13(a) shows the state when the top afocal adapter 5 is attached to the endoscope body 4. FIG. 13(b) shows the state when it is detached. The top afocal adapter 5 is designed and produced to bring emergent rays of respective field angles substantially into parallel rays to an optical axis (i.e. afocal) at the position X, so as to form an image on the image pickup device, when the top afocal adapter is attached. The top afocal adapter type of endoscope is economically advantageous because the expensive endoscope body may be used in common with it. In addition, since the detached section is afocal, the diameter of luminous flux is thick and no real image is formed in the detached section. Thus, the affect of contaminations is practically inconspicuous, and the focal shift caused by misregistration in the attaching operation has an insignificant impact.

In summary, the above discussed prior art systems have an error between the right and left images due to the brightness diaphragm 55 having two apertures. Further, the prior art systems do not describe an end afocal endoscope nor a structure for an adapter type of endoscope. The prior art has the problems of a lengthened rigid section, a disturbed observation by contaminations and an occurrence of reverse-stereoscopic-vision.

SUMMARY OF THE INVENTION

It is an object of the present invention to provide stereoscopic-vision and measurement endoscopes capable of having a short rigid section without any disturbance of contaminations to an observation and any occurrence of reverse-stereoscopic-vision as well as its capability of applying an end afocal adapter.

In order to achieve the aforementioned object, according to one aspect of the present invention, there is provided an endoscope having an insertion part which includes an object optical system to conduct measurements or stereoscopic-vision observations, the object optical system comprising, in turn from an object side to an image side, a first unit, a second unit, a brightness diaphragm, a third unit, and an image pickup unit. The first unit includes an object cover glass, a pair of negative lenses arranged in parallel and almost in contact with each other, and a pair of field masks corresponding to the pair of negative lenses, respectively, wherein a principal ray emergent to the image side in each of the pair of negative lenses is parallel to each optical axis of the pair of negative lenses. The second unit includes a flare mask having an analogous form which corresponds to the range of the field mask, and a first positive lens having an optical axis which is positioned eccentrically to at least one of the optical axes of the pair of negative lenses, wherein the first positive lens forms no real image within the second and third units. The brightness diaphragm includes a single aperture section and an adapter cover glass, the brightness diagram being positioned at a back-focus-position of the first positive lens of the second unit, wherein each optical axis of the pair of negative lenses passes through the single aperture section, the single aperture section being positioned unitarily with the adapter cover glass. The third unit includes a master cover glass, and a second positive lens capable of focusing on an infinity-distance-object, wherein the following equation (1) is satisfied as a condition to enable the second positive lens to focus on the infinity-distance-object:

$$|\phi a/\phi|<0.1 \quad (1)$$

where φa is a combined power of the first unit and the second unit, and φ is an combined power of the first to third units. The image pickup unit includes an infrared cut off filter, and an image pickup device positioned at a back-focus-position of the second positive lens of the third unit, the image pickup device being single and having 2 to 2.5 mm or less of effective image pickup range. Further, the first unit, the second unit, and the brightness diaphragm are comprised in an adapter so as to be detachable from the third unit and the image pickup unit at a boundary between the adapter cover glass and the master cover glass.

According to a second aspect of the present invention, there is also provided an endoscope apparatus including an object optical system to conduct measurements or stereoscopic-vision observations, the object optical system comprising, in turns from an object side to an image side, a first unit, a second unit, a third unit, and an image pickup unit. The first unit includes negative lenses. The second unit includes a first positive lens, wherein the first positive lens forms no real image in the range of the second unit to the third unit. The third unit includes a second positive lens. The image pickup unit includes a single image pick up device.

In the second aspect of the present invention, the second positive lens of the third unit may be capable of approximately focusing on an infinity-distance-object, wherein the following equation (1) is satisfied as a condition to approximately enable the second positive lens to focus on the infinity-distance-object:

$$|\phi a/\phi|<0.1 \quad (1)$$

where φa is a combined power of the first unit and the second unit, and φ is an overall combined power of the first to third units. The endoscope apparatus may further include a brightness diaphragm having a single aperture section, and the brightness diaphragm may be positioned approximately at a back-focus-position of the first positive lens of the second unit.

Further, the negative lenses of the first unit may be a pair of negative lenses arranged in parallel and almost in contact with each other, and the first positive lens may have an optical axis positioned eccentrically to at least one of the optical axes of the pair of negative lenses.

In this case, the pair of negative lenses may include a lens having a concave surface which is directed to the object side. Further, the pair of negative lenses may include a pair of first concave lenses and a pair of second concave lenses, wherein the pair of first concave lenses is either a single lens or cemented lens, which has a concave surface as a final surface on the image side, the concave surface being directed to the image side, and the pair of second concave lenses is either a single lens or cemented lens, which has a convex surface as a final surface on the image side, the convex surface being directed to the image side.

The pair of negative lenses may have a cutout portion at their circumferences, wherein each of said negative lenses abuts with each other at the cutout portion such that the distance between the centers of the circumferences is less than the sum of the radii thereof.

In the second aspect of the present invention, the endoscope apparatus may further include a brightness diaphragm having two aperture sections, the brightness diaphragm being positioned either at the object side or at the image side within the second unit. The negative lenses of the first unit may include a pair of negative lenses arranged in parallel and almost in contact with each other, and the first positive lens has an optical axis which is positioned eccentrically to at least one of the optical axes of the pair of negative lenses. The first positive lens may include a first lens and second lens, wherein the first lens is a positive power lens and has a convex surface directed to and located proximately to the object side, and the second lens is a negative power lens and has a concave surface directed to and located proximately to the object side.

In the second aspect of the present invention, the endoscope apparatus may further include an object cover glass provided on the object side in the first unit, a prism provided on the object side in the first unit to convert a line of sight, a field mask provided in the first unit, the field mask corresponding to the negative lenses, a flare mask provided in the second unit, or a master cover glass provided proximally to the object side in the third unit.

Further, the first unit and the second unit may be comprised in an adapter so as to be detachable to the third unit and the image pickup unit. In this case, the endoscope apparatus may further include a brightness diaphragm and an adapter cover glass unitarily positioned with the brightness diaphragm. The image pickup device may be positioned at a back-focus-position of the second positive lens of the third unit, and the image pickup device is singe and has 2 to 2.5 mm or less of effective image pickup range.

Other features and advantages of the present invention will be apparent from the accompanying drawings and from the detailed description.

BRIEF DESCRIPTION OF THE DRAWINGS

FIG. 3 is a sectional view showing an optical system according to a third embodiment of the present invention.

FIG. 4 is a sectional side elevation view showing the optical system according to the third embodiment of the present invention.

DETAILED DESCRIPTION OF THE PREFERED EMBODIMENT

Figure 1:
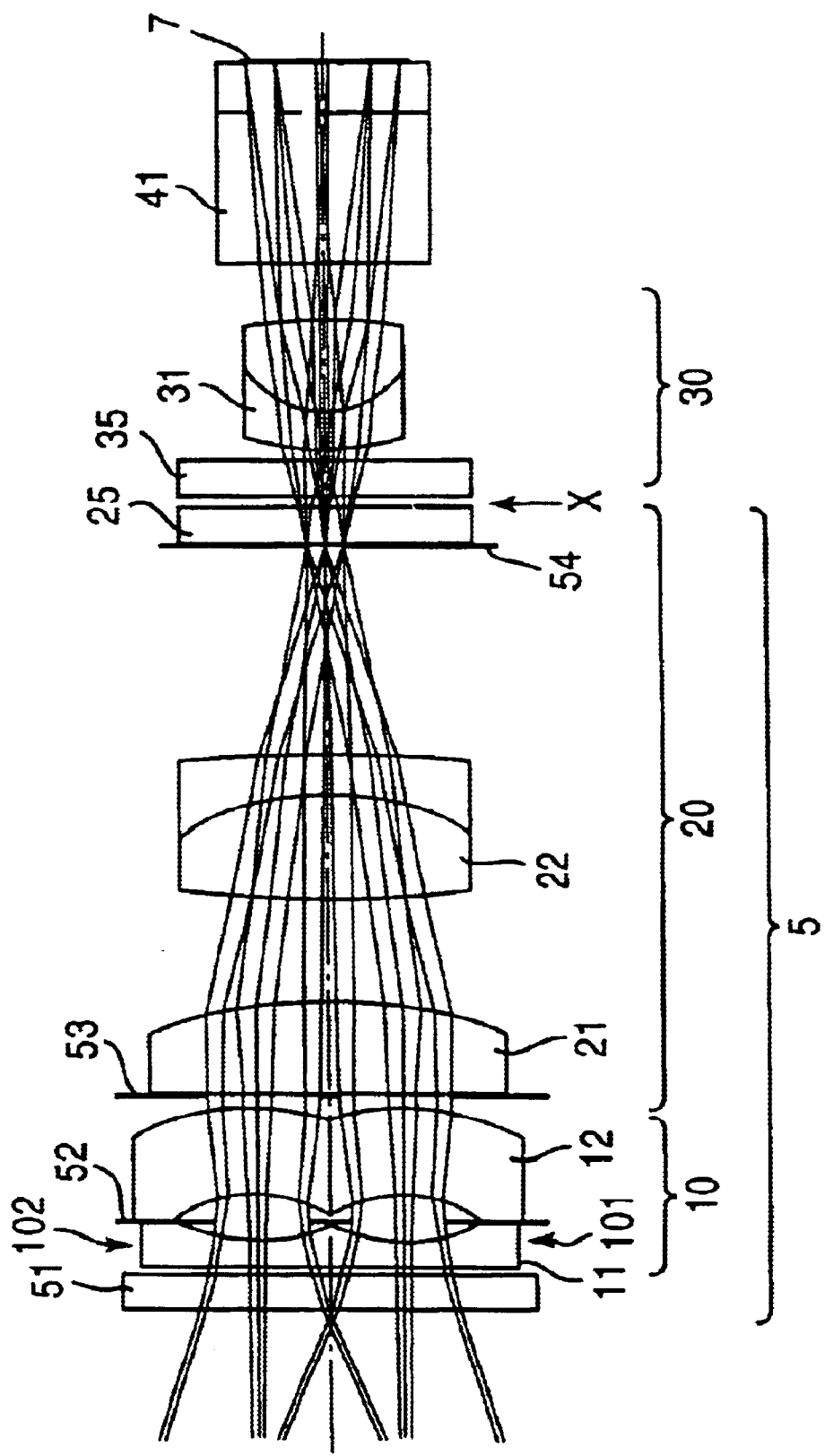
FIG. 1 is a sectional view showing an optical system according to a first embodiment of the present invention.

FIG. 1 shows the overall construction of an object optical system in an endoscope according to the first embodiment of the present invention. The construction of this embodiment comprises, in turn from the object side, a cover glass 51 for protecting from water and dust, a first unit 10 including a pair of negative lenses 101 and 102 which have the same negative power respectively and are arranged side by side and in parallel with each other, a second unit 20 including positive power lenses, a third unit 30 including a positive power lens and a single imaging pickup device 7 as an image pickup or imaging means. Each of the two images have a field angle of 60° and a Fno. of 6.3, respectively, wherein Fno is an effective F-number of an optical system.

Figure 7:
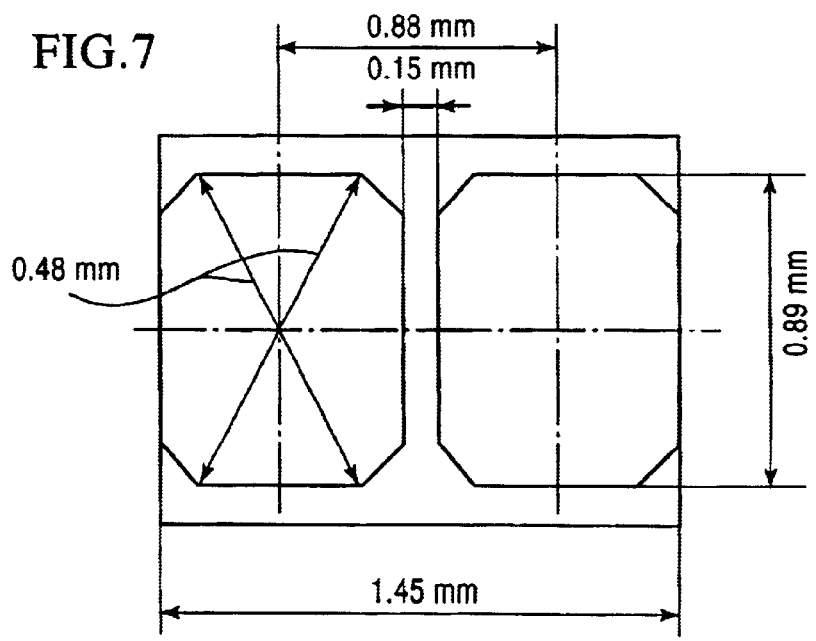
FIG. 7 is an enlarged end view showing a field range on an image pickup device in each embodiment.

The negative lenses of the first unit 10 comprises, in turn from the object side, plane-concave lenses 11 having a concave surface directed to the image side, and meniscus concave lenses 12 having a convex surface directed to the image side. A field range is defined in between the plane-concave lenses 11 and the meniscus concave lenses 12, and a field mask 52 having an analogous form to this field range is interposed in therebetween. The field range has a form and size as shown in FIG. 7 on the image pickup device. In the two pairs of lenses 101 and 102, the distance between lines (i.e. optical axes) respectively passing through the centers of curvature of the respective lens surfaces is 1.46 mm. The lenses 101 and 102 also have respective inner side surfaces which are arranged in parallel and almost in contact with each other and processed in a D shape so as to allow the lenses 101 and 102 to be arranged closer in parallel. The negative power ($\phi 1$) of the two pairs of lenses 101 and 102 is −0.602 by the gross.

The second unit 20 comprises, in turn from the object side, a plane-convex lens 21 having a convex surface directed to the image side, a concave-convex cemented lens 22, a brightness diaphragm 54 including an aperture section provided to be used commonly by the two pairs of lenses 101 and 102 of the first unit, and a cover glass 25 in contact with the brightness diaphragm 54. The positive power ($\phi 2$) of the second unit is 0.232 by the gross. An optical axis (i.e. a line connecting centers of curvature of respective lens surfaces) of the second unit is decentered, or eccentrically positioned, by 0.73 mm respectively to the optical axes of the two pairs of lenses of the first unit. The position of the brightness diaphragm 54 is defined at a back-focus-position of the overall second unit. A light shielding sheet or flare mask 53 is further provided which contacts with the flat surface of the plane-convex lens 21 of the second unit. The flare mask 53 effectively cuts off a flare generated in the edge thickness and at the edge of the two pairs of lenses of the first unit. An opening of the flare mask 53 has an analogous shape to the field range of FIG. 7.

On the other hand, a combined power is shown as follows. The paraxial tracing is applied to compute the combined power. This computing is carried out under the condition that the optical axis of the first unit is overlapped over the optical axes of the second and third units by shifting the decentered optical axis of the first unit. As the result of the computing, the combined power $\phi a$ (0.0263) of the first and second units to the overall power $\phi(1.03)$ of the first to third units is determined as:

$$\phi a/\phi = 0.026$$

Here, it may be considered that $\phi a/\phi = 0$ means a fully afocal state, and $\phi a/\phi < 0.1$ means an approximately afocal state. Thus, an emergent luminous flux of each field angle in the second unit becomes afocal.

The third unit 30 comprises, in turn from the object side, a cover glass 35 and a concave-convex cemented lens 31. This third unit has 0.389 of positive power ($\phi 3$) by the gross. The third unit 30 is positioned on the object side to the image pickup device 7 with which an infrared cut off filter 41 is coupled. The optical axis of the third unit lies on the same line as the optical axis of the second unit. When looking from the side of the image pickup device, the orientation of this optical axis is arranged to focus approximately at infinity only by the third unit.

A process of forming an image in the optical system of the first embodiment will now be described.

Rays from an object is first taken in with a desired field angle through the plane-concave lenses 11, as negative lenses in the first unit. Then, by the action of the second meniscus concave lenses 12, a principal ray emergent from the first unit in each field angle is parallelized approximately to the optical axis so as to make an exit pupil of the first unit lie approximately at infinity. In the second unit, the brightness diaphragm 54 is placed near a back-focus-position so that an entrance pupil of the second unit may lie approximately at infinity.

Thus, the rays passed through the first unit may be transmitted to the third unit via the single common aperture of the brightness diaphragm 54 without any restriction. The luminous flux from the second unit 20 is an afocal luminous flux so that two images having parallax to one object may be generated on the image pickup device 7 by making the luminous flux from the second unit 20 pass through the third unit 30 having the focal point adjusted to lie at infinity.

Figure 8:
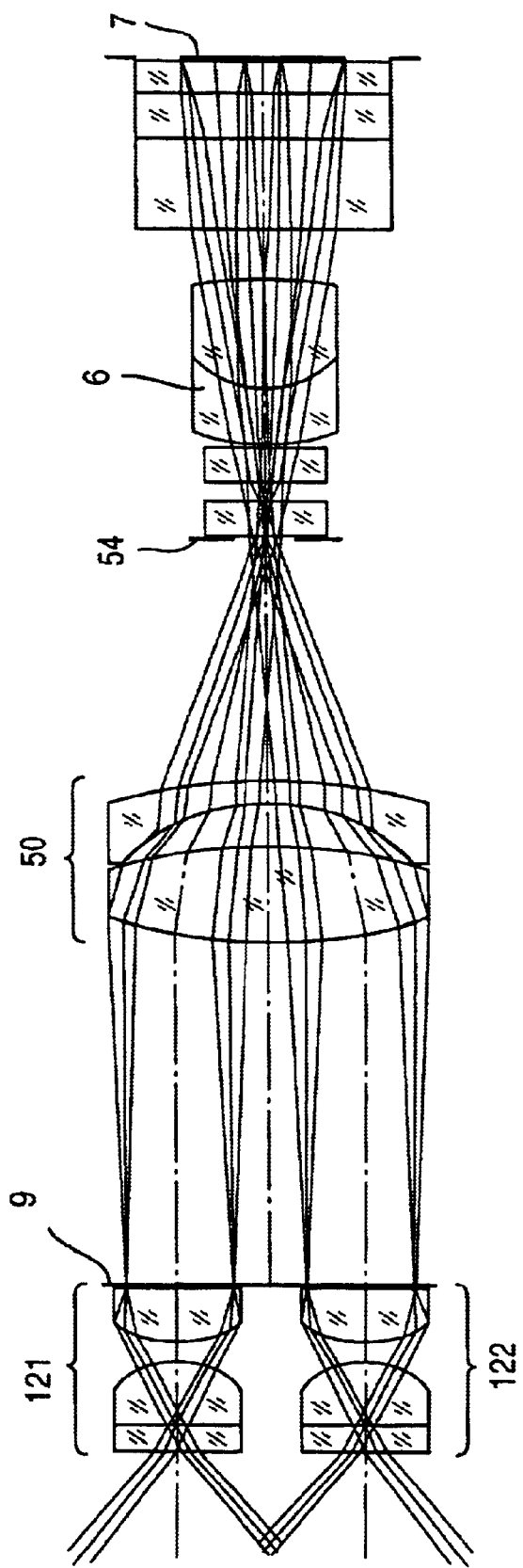
FIG. 8 is a sectional view showing an optical system according to the prior art.
Figure 11:
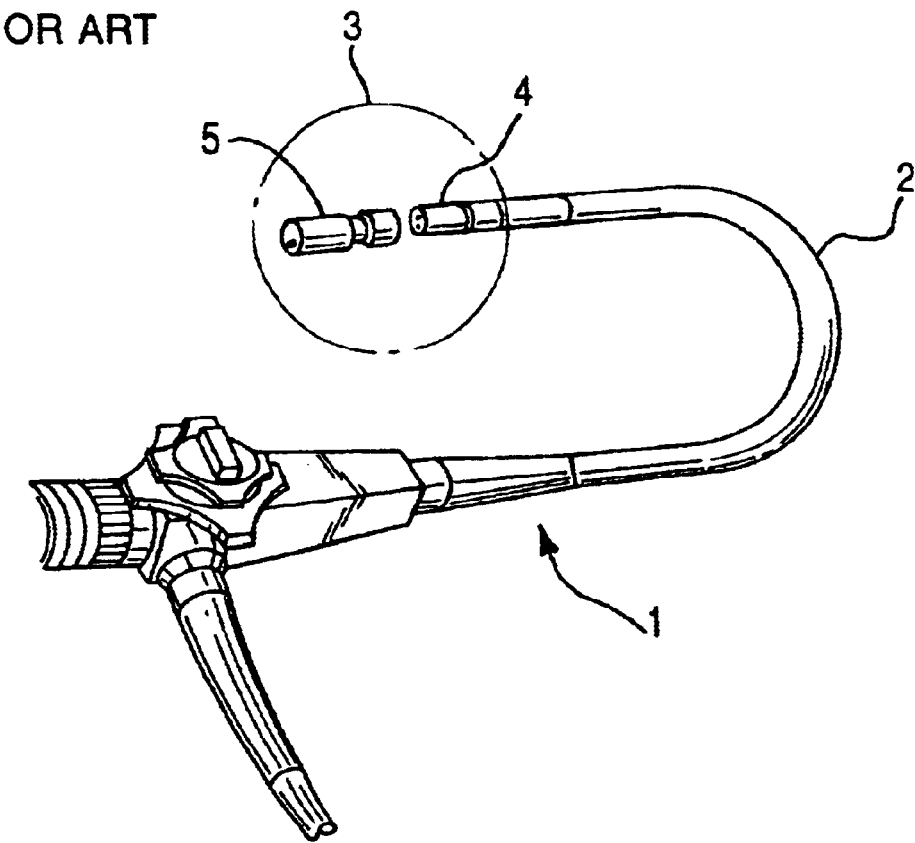
FIG. 11 is a perspective view showing an exterior appearance of a top afocal adapter type of an endoscope apparatus.
Figure 12:
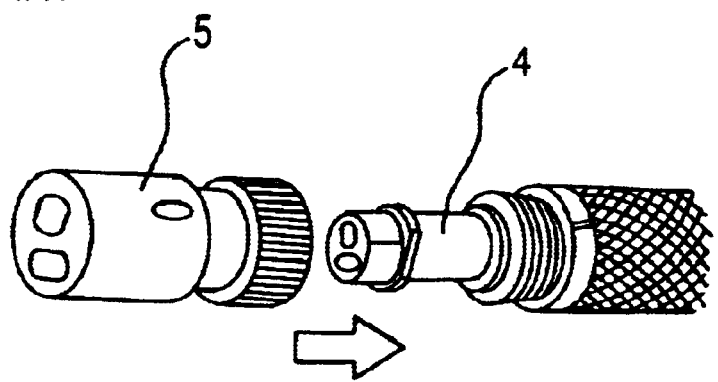
FIG. 12 is a perspective view showing a top section of the top afocal adapter type of endoscope apparatus.
Figure 13A:
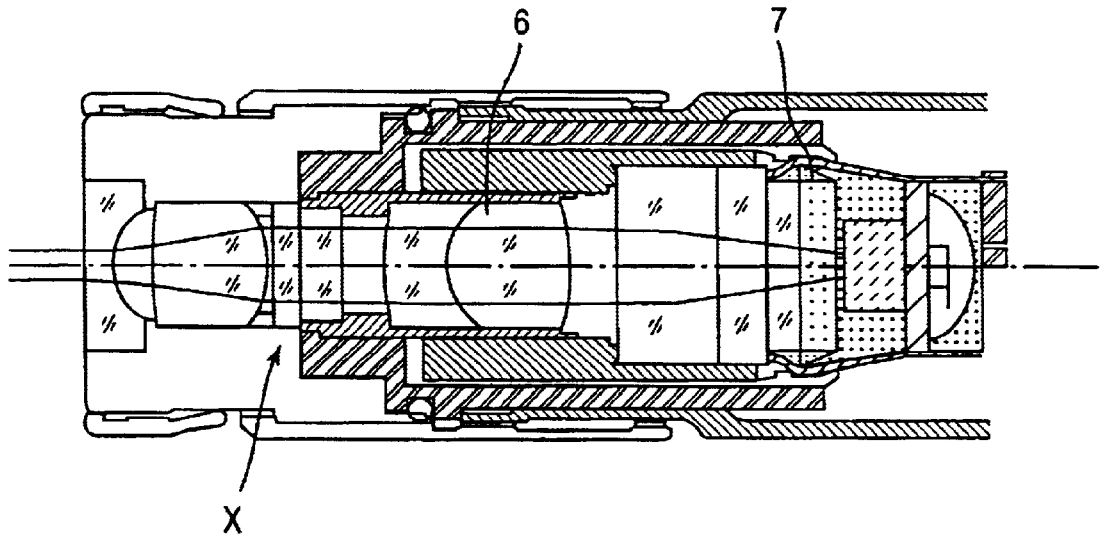
FIGS. 13(a) and (b) show the states in which the adapter is attached and detached, respectively.
Figure 13B:
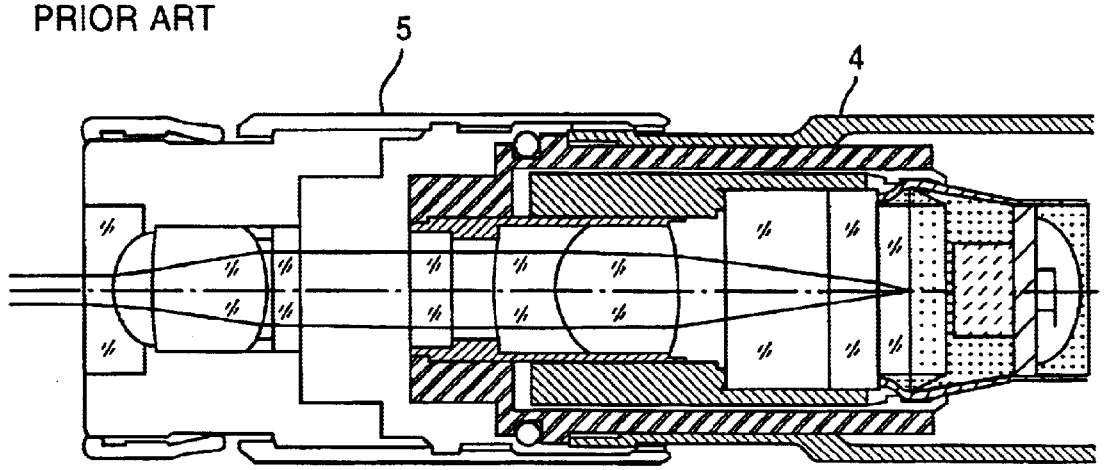

The third unit 30 and the image pickup device 7 are stationarily located in an endoscope body, and typically the first to third units 10, 20 and 30, the cover glass 51, and the image pickup device 7 are fixed to the endoscope body. Otherwise, it may be contemplated that the first and second units are adapted to be detachable to the endoscope body as a top afocal adapter. In the embodiment shown in FIG. 1, there is provided an endoscope having a top afocal adapter 5 which is changed at a position shown by X to use depending on various applications. In such a construction, a detached section corresponds to the afocal luminous flux section so that the affect of contaminations is practically inconspicuous and the focal shift caused by misregistration of this detachable mechanism may be minimized. In this embodiment, the second and third units forming two images for stereoscopic-vision are common parts and the aperture of the brightness diaphragm is also common, so that the error of right and left images may be further reduced. In addition, the first unit of this embodiment is negative lenses so that the length of the first unit may be shorter than the prior art system (FIG. 8) having the first unit of positive lenses focusing into real images, which allows the rigid section to be shortened.

The meniscus concave lenses 12 of the first unit, which has a convex surface directed to the image side, has the shape of an approximate concentric circle because the curvature centers of its surfaces are adjacent to each other. Thus, when it is difficult to control the eccentricity of the outer diameter in a manufacturing process, a processing and assembling method may be contemplated in which a plane-concave lens and a plane-convex lens are separately produced and then coupled into one part.

The term referred to as "lens" herein is intended to mean any combination of a plurality of "single lens" or cemented lens, as well as any combination thereof.

Figure 14:
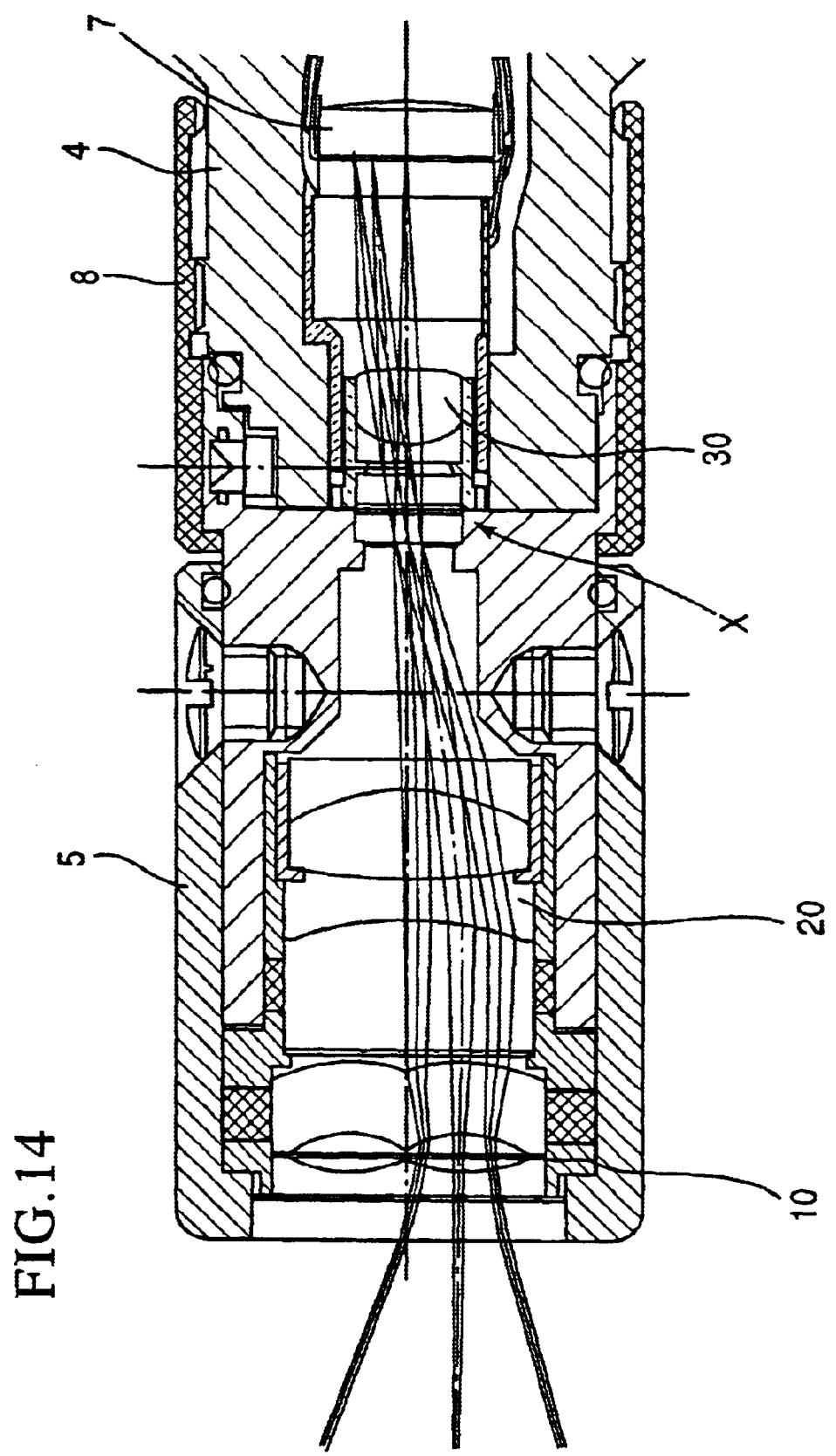
FIG. 14 is a sectional view showing an adapter frame construction mounted with this optical system of the top afocal adapter type of endoscope apparatus according to a first embodiment of the present invention.

FIG. 14 shows one example of an overall adapter frame construction mounted with this optical system. The first unit 10 and the second unit 20 are provided in the top afocal adapter 5, and the third unit 30 is provided at the top section of the endoscope apparatus body 4. The adapter 5 is detachable at the position X by screws of a knurled nut 8.

Lenses data of the first embodiment is as follows.

| Field angle: 60° | Fno.: 6.3 |
|---|---|

The third to sixth surfaces belong to the first unit, and the distance between the pair of negative lenses is 1.46 mm.

The seventh to fourteenth surfaces belong to the second unit, and the eccentric distance to the two pair of negative lenses of the first unit is 0.73 mm.

The fifteenth to nineteenth surfaces belong to the third unit.

| $\phi 1$: −0.602 | $\phi 2$: 0.232 | $\phi 3$: 0.389 | |
|---|---|---|---|
| $\phi a$: 0.0263 | $\phi$: 1.03 | $\phi a/\phi$: 0.026 | |
| R: curvature radius, d: spacing, n: refraction factor, γ: Abbe number ||||

| face-object | R | d | n | γ |
|---|---|---|---|---|
| distance |  | 11.5000 |  |  |
| 1 | INF | 0.4000 | 1.51633 | 64.1 |
| 2 | INF | 0.0500 |  |  |
| 3 | INF | 0.3000 | 1.88300 | 40.8 |
| 4 | 1.75546 | 0.5000 |  |  |
| 5 | −1.27304 | 0.9500 | 1.88300 | 40.8 |
| 6 | −2.23382 | 0.1530 |  |  |
| 7 | INF | 1.0000 | 1.77250 | 49.6 |
| 8 | −4.59900 | 1.1132 |  |  |
| 9 | 12.48876 | 1.2000 | 1.72916 | 54.7 |
| 10 | −2.22927 | 0.4000 | 1.80518 | 25.4 |
| 11 | −12.78262 | 2.3216 |  |  |
| (brightness diaphragm) | INF | 0.0300 |  |  |
| 13 | INF | 0.4000 | 1.51633 | 64.1 |
| 14 | INF | 0.1000 |  |  |
| 15 | INF | 0.4000 | 1.51633 | 64.1 |
| 16 | INF | 0.1000 |  |  |
| 17 | 2.36086 | 0.4000 | 1.84666 | 23.8 |

-continued

| $\phi 1$: −0.602 | $\phi 2$: 0.232 | $\phi 3$: 0.389 | |
|---|---|---|---|
| $\phi a$: 0.0263 | $\phi$: 1.03 | $\phi a/\phi$: 0.026 | |
| R: curvature radius, d: spacing, n: refraction factor, γ: Abbe number ||||

|  | | | | |
|---|---|---|---|---|
| 18 | 0.87942 | 1.0000 | 1.72916 | 54.7 |
| 19 | −3.74638 | 0.6003 |  |  |
| 20 | INF | 1.6000 | 1.51400 | 75.0 |
| 21 | INF | 0.5000 | 1.49700 | 81.6 |
| 22 (surface of imaging pickup device) | INF | 0.0300 |  |  |

Figure 2:
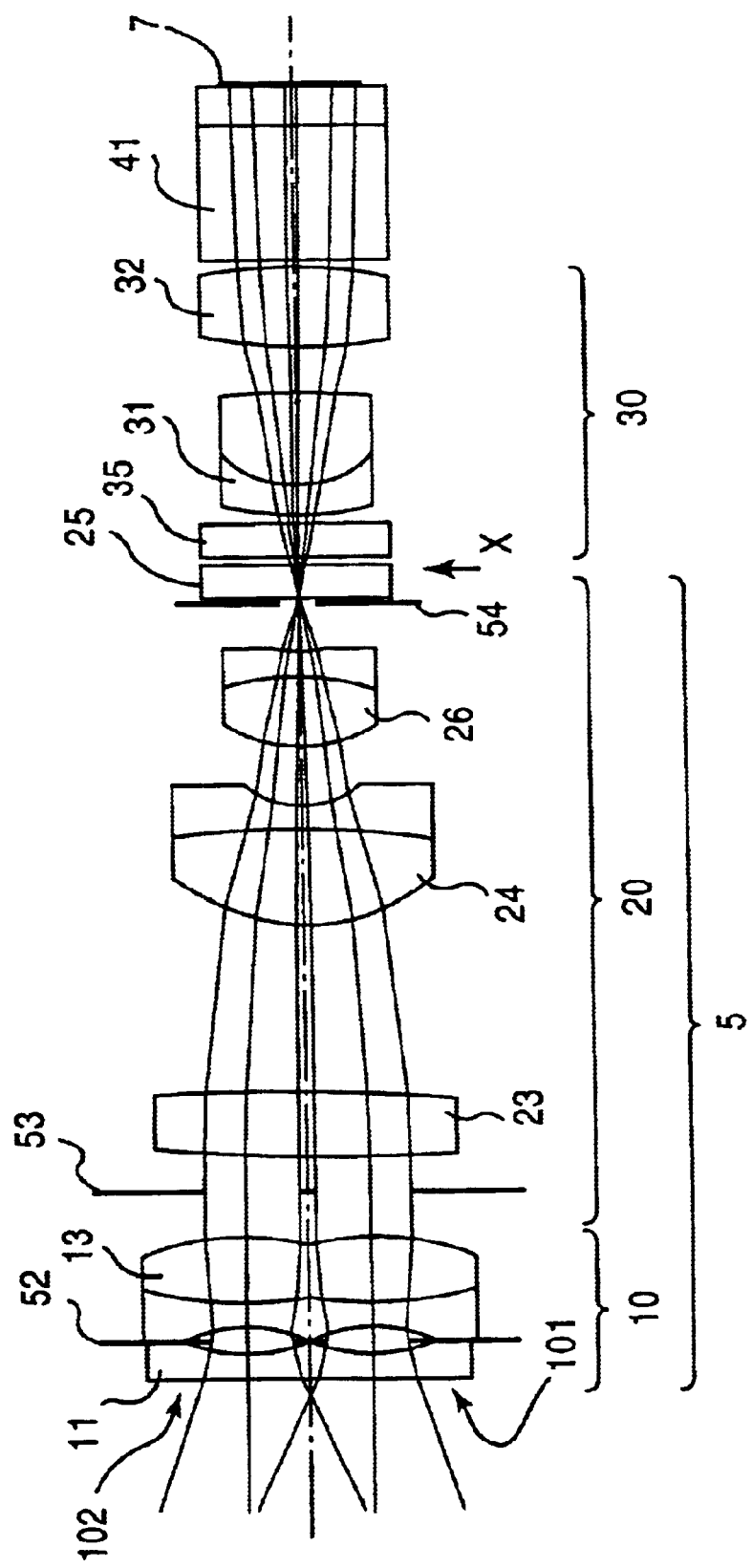
FIG. 2 is a sectional view showing an optical system according to a second embodiment of the present invention.

FIG. 2 shows a construction of the object optical system in an endoscope according to the second embodiment of the present invention. This embodiment differs from the first embodiment to the extent that there is no cover glass at the top thereof and each of the lenses structures of the first to third units are different. These differences will now be described.

Two images have 65° of field angle and 6.4 of Fno., respectively. The negative lenses of the first unit 10 comprises, in turn from the object side, plane-concave lenses 11 having a concave surface directed to image side, and cemented lenses 13 which is composed of biconcave lenses and biconvex lenses and has negative power by the gross. A field mask 52 is interposed in between the plane-concave lenses 11 and the cemented lenses 13. The distance between the optical axes of the parallelized negative lenses is 1.46 mm, and the negative power ($\phi 1$) is −0.641 by the gross.

The second unit 20 comprises, in turn from the object side, a biconvex lens 23, a concave-convex cemented lens 24 having negative power by the gross, a concave-convex cemented lens 26 having positive power by the gross, a brightness diaphragm 54 including an aperture section provided to be used commonly by the two parts of lenses positioned in parallel with each other in the first unit, and a cover glass 25 contacted with the brightness diaphragm 54. The positive power ($\phi 2$) is 0.234 by the gross. An optical axis of the second unit is decentered by 0.73 mm respectively to the optical axes of the two pairs of lenses of the first unit.

A combined power $\phi a$ (0.0282) of the first and second units to the overall power $\phi$(1.07) of the first to third units is determined as:

$$\phi a/\phi = 0.026$$

Thus, an emergent luminous flux of each field angle in the second unit becomes approximately afocal.

The third unit 30 comprises, in turn from the object side, a cover glass 35 and a concave-convex cemented lens 31, and a biconvex lens 32. This third unit has 0.388 of positive power by the gross ($\phi 3$).

The imaging in the second embodiment is characterized in that the occurrence of a chromatic aberration may be restrained because of the cemented lenses which has negative power by the gross. Further, the second unit is comprised of a group of three lenses including a group of negative lenses so that astigmatism and curvature of a field may be sufficiently corrected. The third unit is also comprised of a group of two lenses so that the third unit may be satisfactorily corrected for aberration independently.

Lenses data of the second embodiment is as follows.

| Field angle: 65° | Fno.: 6.4 |
|---|---|

The first to fifth surfaces belong to the first unit, and the distance between the pair of negative lenses is 1.46 mm.

The sixth to sixteenth surfaces belong to the second unit, and the eccentric distance to the two pair of negative lenses of the first unit is 0.73 mm.

The seventeenth to twenty third surfaces belong to the third unit.

| φ1: −0.641 | φ2: 0.234 | φ3: 0.388 | |
|---|---|---|---|
| φa: 0.0282 | φ: 1.07 | φa/φ: 0.026 | |
| R: curvature radius, d: spacing, n: refraction factor, γ: Abbe number | | | |

| face-object | R | d | n | γ |
|---|---|---|---|---|
| distance | | 10.3938 | | |
| 1 | INF | 0.3000 | 1.83481 | 42.7 |
| 2 | 1.92150 | 0.3529 | | |
| 3 | −1.48425 | 0.3000 | 1.83481 | 42.7 |
| 4 | 4.85836 | 0.8000 | 1.69895 | 30.1 |
| 5 | −2.70463 | 1.0204 | | |
| 6 | 16.94334 | 0.8000 | 1.88300 | 40.8 |
| 7 | −24.31827 | 2.0375 | | |
| 8 | 2.23356 | 1.2000 | 1.77250 | 49.6 |
| 9 | −10.41313 | 0.3000 | 1.59270 | 35.3 |
| 10 | 1.06742 | 0.7941 | | |
| 11 | 1.64417 | 0.8800 | 1.77250 | 49.6 |
| 12 | −2.50406 | 0.3200 | 1.64769 | 33.8 |
| 13 | 1.76130 | 0.61800 | | |
| (brightness diaphragm) | INF | 0.0300 | | |
| 15 | INF | 0.4000 | 1.51633 | 64.1 |
| 16 | INF | 0.1000 | | |
| 17 | INF | 0.4000 | 1.51633 | 64.1 |
| 18 | INF | 0.1000 | | |
| 19 | 3.87761 | 0.4000 | 1.84666 | 23.8 |
| 20 | 1.30626 | 1.1000 | 1.72000 | 50.2 |
| 21 | −11.89684 | 0.6003 | | |
| 22 | 4.64203 | 1.0000 | 1.77250 | 49.6 |
| 23 | −5.57008 | 0.1000 | | |
| 24 | INF | 1.6000 | 1.54100 | 75.0 |
| 25 | INF | 0.5000 | 1.49700 | 81.6 |
| 26 (surface of imaging pickup device) | INF | 0.0300 | | |

FIGS. 3 and 4 shows a construction of the object optical system according to the third embodiment of the present invention, wherein FIG. 4 is a side view of FIG. 3. This embodiment is different from the first embodiment in that a prism 56 is provided as a substitute for the cover glass to change the direction of observation, a first unit being composed only of a single-plane concave lenses having a concave surface directed to the object side, and a third unit having the same construction as the second embodiment. Particular constructions and effects will now be described.

The first unit is composed only of a single plane-concave lenses 14 having a concave surface directed to the object side, so that cost reduction may be facilitated and assembling efficiency enhanced, due to the reduced number of parts. Further, when two plane-concave lenses are produced all at once as glass molded lenses formed by press die rather than a method in which two plane-concave lenses positioned in parallel with each other and polished separately and then assembled, the cost reduction may be advantageously facilitated.

In addition, the field mask 52 is located on the flat surface side of the plane-concave lenses in the first unit so that the action of the flare cut off mask 53 for cutting off flare as described in the first and second embodiments may be combined. This is advantageous to achieving a simple construction.

Lenses data of the third embodiment is as follows.

| Field angle: 63° | Fno.: 6.3 |
|---|---|

The fourth to fifth surfaces belong to the first unit, and the distance between the pair of negative lenses is 1.46 mm.

The sixth to thirteen surfaces belong to the second unit, and the eccentric distance to the pair of negative lenses of the first unit is 0.73 mm.

The fourteenth to twentieth surfaces belong to the third unit.

| φ1: −0.495 | φ2: 0.234 | φ3: 0.388 | |
|---|---|---|---|
| φa: 0.0324 | φ: 0.826 | φa/φ: 0.039 | |
| R: curvature radius, d: spacing, n: refraction factor, γ: Abbe number | | | |

| face-object | R | d | n | γ |
|---|---|---|---|---|
| distance | | 8.5000 | | |
| 1 | INF | 2.2000 | 1.88300 | 40.8 |
| 2 | INF | 2.2000 | 1.88300 | 40.8 |
| 3 | INF | 0.4500 | | |
| 4 | −1.78343 | 0.5000 | 1.88300 | 40.8 |
| 5 | INF | 2.0323 | | |
| 6 | INF | 1.0000 | 1.77250 | 49.6 |
| 7 | −5.70060 | 0.1000 | | |
| 8 | 4.25418 | 1.2000 | 1.72916 | 54.7 |
| 9 | −6.44107 | 0.4000 | 1.80518 | 25.4 |
| 10 | 9.34839 | 2.7488 | | |
| (brightness diaphragm) | INF | 0.0300 | | |
| 12 | INF | 0.4000 | 1.51633 | 64.1 |
| 13 | INF | 0.1000 | | |
| 14 | INF | 0.4000 | 1.51633 | 64.1 |
| 15 | INF | 0.1000 | | |
| 16 | 3.87761 | 0.4000 | 1.84666 | 23.8 |
| 17 | 1.30626 | 1.1000 | 1.72000 | 50.2 |
| 18 | −11.89684 | 0.6003 | | |
| 19 | 4.64203 | 1.0000 | 1.77250 | 49.6 |
| 20 | −5.57008 | 0.1000 | | |
| 21 | INF | 1.6000 | 1.54100 | 75.0 |
| 22 | INF | 0.5000 | 1.49700 | 81.6 |
| 23 (surface of imaging pickup device) | INF | 0.0300 | | |

Figure 5:
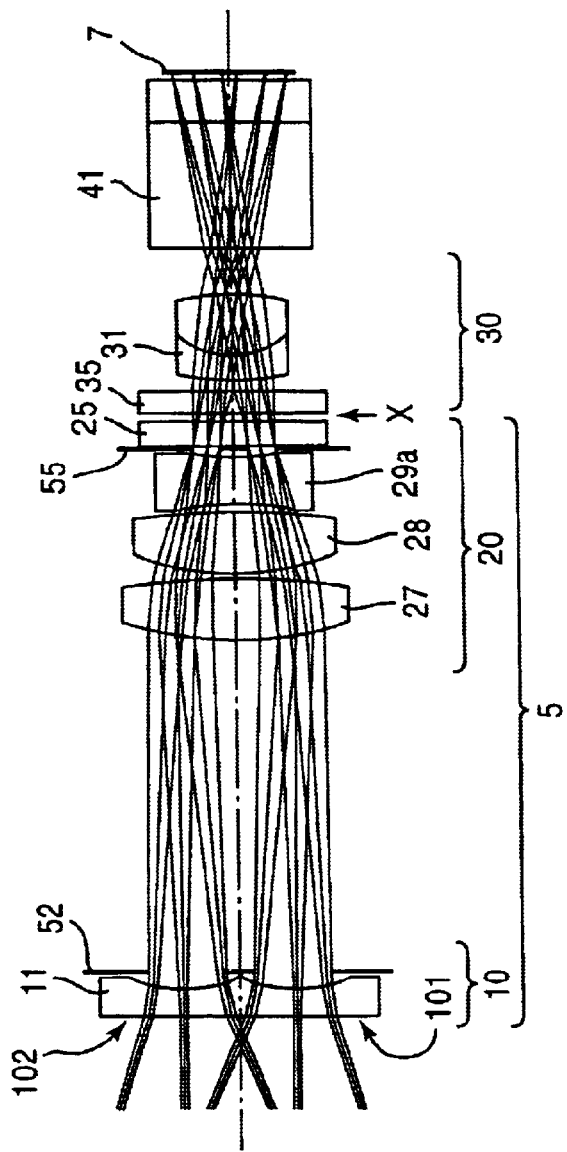
FIG. 5 is a sectional view showing an optical system according to a fourth embodiment of the present invention.

FIG. 5 shows an overall construction of the object optical system in an endoscope according to the fourth embodiment of the present invention. The construction of this embodiment comprises, in turn from the object side, a first unit 10 including two pair of lenses 101 and 102 which have the same negative power respectively and are arranged in parallel with each other, a second unit 20 including positive power lenses, a brightness diaphragm having two aperture sections, a third unit 30 including a positive power lens and an imaging pickup device 7.

The negative lenses of the first unit comprise a single plane-concave lenses having a concave surface directed to the image side, and a field mask 52 provided just after the plane-concave lenses. The distance between the optical axes of the parallelized negative lenses is 1.46 mm, and the negative power (φ1) is −0.610. The field mask doubles with the flare cut off mask 53 for cutting off flare in the first embodiment.

The second unit 20 comprises, in turn from the object side, a biconvex lens 27, a biconvex lens 28, a biconcave lens 29a, and a cover glass 25 for protecting from water and dust. A brightness diaphragm 55 is provided which has two aperture sections and is contacted with the flat surface of the object side of the cover glass 25. The positive power (φ2) is 0.241 by the gross. An optical axis of the second unit is decentered by 0.73 mm respectively to the optical axes of the two pairs of negative lenses of the first unit.

A combined power φa (0.0321) of the first and second units to the overall power φ(1.06) of the first to third units is determined as:

φa/φ=0.030

Thus, an emergent luminous flux of each field angle in the second unit becomes approximately afocal.

The third unit 30 comprises, in turn from the object side, a cover glass 35 and a concave-convex cemented lens 31. The third unit 30 has 0.400 of positive power by the gross (φ3)

Since the second unit comprises, in turn from the object side, two biconvex lenses having positive power and a single biconcave lens having negative power, the ray may approach the optical axes at the exit side of the second unit corresponding to the detached section, and the position of the brightness diaphragm may be lowered. This also allows the outer diameter to be reduced, and the image to be adequately formed without unnecessary reflected light from the adapter attached.

Lenses data of the fourth embodiment is as follows.

| Field angle: 62° | Fno.: 6.8 |
|---|---|

The first to second surfaces belong to the first unit, and the distance between the pair of negative lenses is 1.46 mm.

The third to eleventh surfaces belong to the second unit, and the eccentric distance to the two pair of negative lenses of the first unit is 0.73 mm.

The twelfth to sixteenth surfaces belong to the third unit.

The apertures of the brightness diaphragm are decentered by 0.32 mm to the optical axes of the second unit respectively.

φ1: −0.610    φ2: 0.241    φ3: 0.400
φa: 0.0321    φ: 1.06    φa/φ: 0.030
R: curvature radius, d: spacing, n: refraction factor, γ: Abbe number

| face-object | R | d | n | γ |
|---|---|---|---|---|
| distance |  | 11.7000 |  |  |
| 1 | INF | 0.3000 | 1.83481 | 42.7 |
| 2 | 1.36754 | 4.4836 |  |  |
| 3 | 4.00526 | 0.8000 | 1.72916 | 54.7 |
| 4 | −14.46178 | 0.5000 |  |  |
| 5 | 2.78222 | 0.8000 | 1.77250 | 49.6 |
| 6 | −20.03219 | 0.1000 |  |  |
| 7 | −5.18445 | 0.6000 | 1.64769 | 33.8 |
| 8 | 1.68565 | 0.1500 |  |  |
| (brightness diaphragm) | INF | 0.0300 |  |  |
| 10 | INF | 0.3000 | 1.51633 | 64.1 |
| 11 | INF | 0.1000 |  |  |
| 12 | INF | 0.3000 | 1.51633 | 64.1 |
| 13 | INF | 0.1000 |  |  |
| 14 | 2.32417 | 0.3000 | 1.84666 | 23.8 |
| 15 | 0.95341 | 0.8000 | 1.72916 | 54.7 |
| 16 | −3.97083 | 0.5920 |  |  |
| 17 | INF | 1.6000 | 1.51400 | 75.0 |

-continued

φ1: −0.610    φ2: 0.241    φ3: 0.400
φa: 0.0321    φ: 1.06    φa/φ: 0.030
R: curvature radius, d: spacing, n: refraction factor, γ: Abbe number

| | | | | |
|---|---|---|---|---|
| 18 | INF | 0.5000 | 1.49700 | 81.6 |
| 19 (surface of imaging pickup device) | INF | 0.0700 |  |  |

Figure 6:
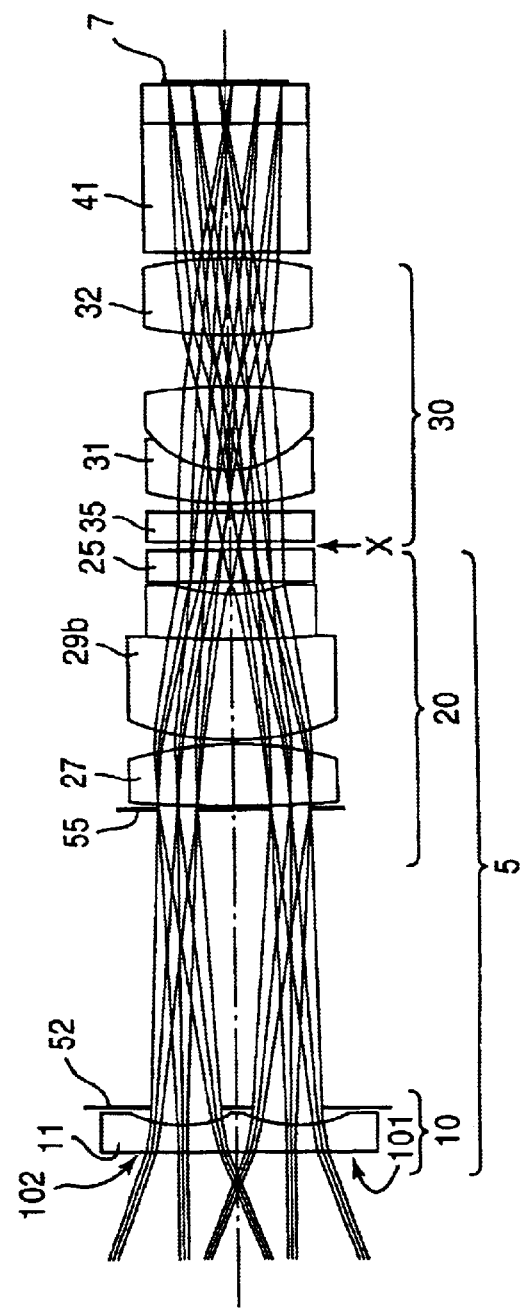
FIG. 6 is a sectional view showing an optical system according to a fifth embodiment of the present invention.
Figure 9:
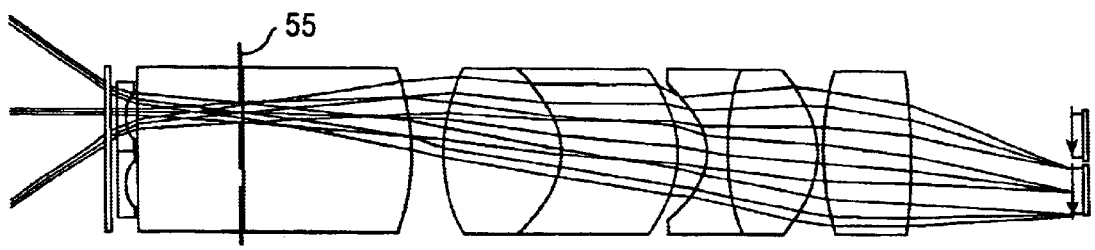
FIG. 9 is a sectional view showing an optical system according to the prior art.
Figure 10:
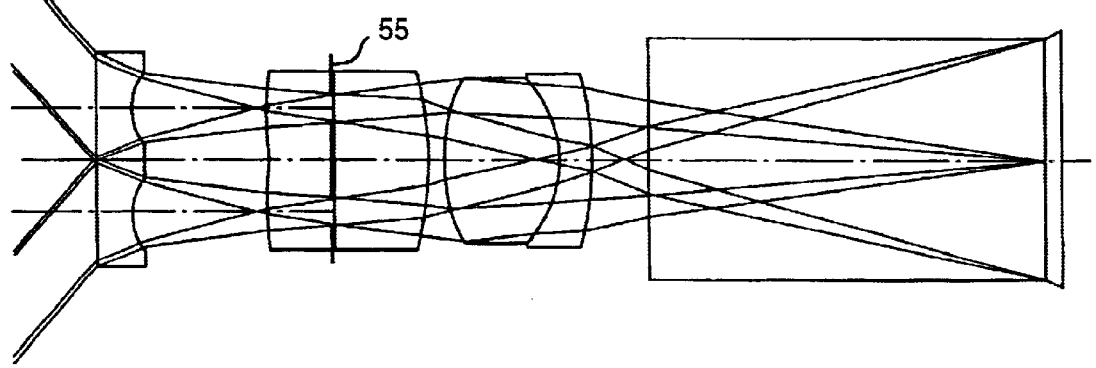
FIG. 10 is a sectional view showing an optical system according to the prior art.

FIG. 6 shows an overall construction of the object optical system of an endoscope according to the fifth embodiment of the present invention. This embodiment differs from the fourth embodiment in terms of the construction of the lenses of the second and third units. This embodiment also differs from the first to fourth embodiments in that the brightness diaphragm 55 is provided proximally to the object side in the second unit. Particular constructions and effects of the fifth embodiment will now be described.

The second unit 20 comprises, in turn from the object side, a brightness diaphragm 55 having two aperture sections, a biconvex lens 27, a cemented lenses 29b including a convex lens having a convex surface on the object side and a concave lens having a concave surface on the image side, and a cover glass 25. It is not necessary to locate the brightness diaphragm at the back-focus-position because the brightness diaphragm has two apertures.

Since the brightness diaphragm 55 is provided proximally to the object side in the second unit, the incident height of the ray is lowered so that the outer diameter of the first unit may be reduced. Further, by virtue of having the cemented lens in the second unit, when the top afocal adapter is attached, the adverse affect of the eccentric error of each of the lenses that occurred in the manufacturing process may be scaled back as compared to the fourth embodiment.

A combined power φa of the first and second units to the overall power φ of the first to third units is determined as:

φa/φ=0.018

This proves that this adapter has an afocal structure.

The third unit comprises, in turn from the object side, a cover glass 35 and negative and positive cemented lens 31, and a biconvex lens 32.

Making up the third unit by the construction of two groups may improve the imaging performance of the master lens and the performance when the adapter is attached.

Lenses data of the fifth embodiment is as follows.

| Field angle: 61° | Fno.: 6.6 |
|---|---|

The first to second surfaces belong to the first unit, and the distance between the pair of negative lenses is 1.46 mm.

The third to tenth surfaces belong to the second unit, and the eccentric distance to the two pair of negative lenses of the first unit is 0.73 mm.

The eleventh to seventeenth surfaces belong to the third unit.

The apertures of the brightness diaphragm are decentered by 0.73 mm to the optical axes of the second unit respectively.

| | | | | |
|---|---|---|---|---|
| φ1: −0.610 | | φ2: 0.231 | φ3: 0.388 | |
| φa: 0.0186 | | φ: 1.04 | φa/φ: 0.018 | |
| R: curvature radius, d: spacing, n: refraction factor, γ: Abbe number | | | | |
| face-object | R | d | n | γ |
| distance | | 11.7000 | | |
| 1 | INF | 0.3000 | 1.83481 | 42.7 |
| 2 | 1.36754 | 4.1111 | | |
| 3 (brightness diaphragm) | INF | 0.0000 | | |
| 4 | 14.47189 | 0.8000 | 1.72916 | 54.7 |
| 5 | −5.45097 | 0.0500 | | |
| 6 | 3.13079 | 1.3000 | 1.77250 | 49.6 |
| 7 | 9.87579 | 0.5500 | 1.64769 | 33.8 |
| 8 | 1.88234 | 0.1549 | | |
| 9 | INF | 0.4000 | 1.51633 | 64.1 |
| 10 | INF | 0.1000 | | |
| 11 | INF | 0.4000 | 1.84666 | 23.8 |
| 12 | INF | 0.1000 | | |
| 13 | 3.87761 | 0.4000 | 1.84666 | 23.8 |
| 14 | 1.30626 | 1.1000 | 1.72000 | 50.2 |
| 15 | −11.89684 | 0.6003 | | |
| 16 | 4.64203 | 1.0000 | 1.77250 | 49.6 |
| 17 | −5.57008 | 0.1000 | | |
| 18 | INF | 1.6000 | 1.51400 | 75.0 |
| 19 | INF | 0.5000 | 1.49700 | 81.6 |
| 20 | INF | 0.0300 | | |
| 21 (surface of imaging pickup device) | INF | | | |

As is apparent from the above description, the present invention may provide stereoscopic-vision and measurement endoscopes capable of having a short rigid section without any disturbance of contaminations to an observation and any uncomfortable feeling on the right and left images as well as its capability of applying an end afocal adapter.

What is claimed is:

1. An endoscope apparatus including an object optical system to conduct measurements or stereoscopic observations, said object optical system comprising:
   in turn from an object side to an image side, a first unit, a second unit, a third unit, and an image pickup unit;
   wherein said first unit includes a pair of negative lenses arranged side by side;
   said second unit including a first positive lens, wherein said first positive lens forms no real image within said second and third units;
   said third unit including a second positive lens; and
   said image pickup unit including a single image pick up device,
   wherein said second positive lens of said third unit is capable of approximately focusing on an infinity-distance-object, wherein the following equation is satisfied as a condition to approximately enable said second positive lens to focus on the infinity-distance-object:

$$|\varphi a/\varphi| < 0.1 \quad (1)$$

where φa is a combined power of said first unit and said second unit, and φ is a combined power of said first to third units.

2. The endoscope apparatus according to claim 1, which further includes a brightness diaphragm having a single aperture section, wherein said brightness diaphragm is positioned approximately at a back-focus-position of said first positive lens of said second unit.

3. The endoscope apparatus according to claim 2, wherein said pair of negative lenses are arranged in parallel, and said first positive lens has an optical axis positioned eccentrically to at least one of the optical axes of said pair of negative lenses.

4. The endoscope apparatus according to claim 3, wherein said pair of negative lenses includes a lens having a concave surface which is directed to said object side.

5. The endoscope apparatus according to claim 3, wherein each negative lens of said pair of negative lenses of said first unit includes a first concave lens and a second concave lens, wherein said first concave lens is either a single lens or cemented lens, which has a concave surface as a final surface on said image side, said concave surface being directed to said image side, and said second concave lens is either a single lens or cemented lens, which has a convex surface as a final surface on said image side, said convex surface being directed to said image side.

6. The endoscope apparatus according to claim 5, wherein said pair of negative lenses have a cutout portion at their circumferences, wherein each of said negative lenses abuts with each other at said cutout portion such that the distance between the centers of said circumferences is less than the sum of the radii thereof.

7. The endoscope apparatus according to claim 1, which further includes a brightness diaphragm having two apertures sections, said brightness diaphragm being positioned either at said object side or at said image side within said second unit.

8. The endoscope apparatus according to claim 7, wherein said negative lenses of said first unit includes a pair of negative lenses arranged in parallel said first positive lens has an optical axis which is positioned eccentrically to at least one of the optical axes of said pair of negative lenses.

9. The endoscope apparatus according to claim 8, wherein said pair of negative lenses have a cutout portion at their circumferences, wherein each of said negative lenses abuts with each other at said cutout portion such that the distance between the centers of said circumferences is less than the sum of the radii thereof.

10. The endoscope apparatus according to claim 8, wherein said first positive lens includes a first lens and second lens, wherein first lens is a positive power lens and has a convex surface directed to and located proximately to said object side, and said second lens is a negative power lens and has a concave surface directed to and located proximately to said object side.

11. The endoscope apparatus according to claim 1, which further includes an object cover glass provided on said object side in said first unit.

12. The endoscope apparatus according to claim 1, which further includes a prism provided on said object side in said first unit to convert a line of sight.

13. An endoscope apparatus including an object optical system to conduct measurements or stereoscopic observations, said object optical system comprising:
   in turn from an object side to an image side, a first unit, a second unit, a third unit, and an image pickup unit;
   wherein said first unit includes a pair of negative lenses arranged side by side;
   said second unit including first positive lens, wherein said first positive lens forms no real image within said second and third units;
   said third unit including second positive lens; and
   said image pickup unit including a single image pick up device;

said endoscope apparatus further includes a field mask in said first unit, said field mask corresponding to said negative lenses.

14. The endoscope apparatus according to claim 1, which further including a flare mask provided in said second unit.

15. An endoscope apparatus including an object optical system to conduct measurements or stereoscopic observations, said object optical system comprising:

in turn from an object side to an image side, a first unit, a second unit, a third unit, and an image pickup unit;

wherein said first unit includes a pair of negative lenses arranged side by side;

said second unit including first positive lens, wherein said first positive lens forms no real image within said second and third units;

said third unit including second positive lens; and said image pickup unit including a single image pick up device;

wherein said first unit and said second unit are comprised in an adapter so as to be detachable from said third unit and said image pickup unit.

16. The endoscope apparatus according to claim 15, which further including a brightness diaphragm and an adapter cover glass unitarily positioned with said brightness diaphragm.

17. The endoscope apparatus according to claim 15, which further including a master cover glass provided proximally to said object side in said third unit.

18. An endoscope apparatus including an object optical system to conduct measurements or stereoscopic observations, said object optical system comprising:

in turn from an object side to an image side, a first unit, a second unit, a third unit, and an image pickup unit;

wherein said first unit includes a pair of negative lenses arranged side by side;

said second unit including first positive lens, wherein said first positive lens forms no real image within said second and third units;

said third unit including second positive lens; and said image pickup unit including a single image pick up device;

wherein said image pickup device is positioned at a back-focus-position of said second positive lens of said third unit, and said image pickup device is single and has 2 to 2.5 mm or less of effective image pickup range.

* * * * *